United States Patent
Mannheimer et al.

[11] Patent Number: 5,995,856
[45] Date of Patent: *Nov. 30, 1999

[54] NON-CONTACT OPTICAL MONITORING OF PHYSIOLOGICAL PARAMETERS

[75] Inventors: Paul D. Mannheimer, Danville; Michael E. Fein, Mountain View, both of Calif.

[73] Assignee: Nellcor, Incorporated, Pleasanton, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/562,169

[22] Filed: Nov. 22, 1995

[51] Int. Cl.⁶ .................................................. A61B 5/00
[52] U.S. Cl. ................................. 600/322; 600/323
[58] Field of Search ........................ 128/633, 664, 128/665, 666; 356/41; 600/322, 323, 326, 330, 336, 340, 473, 476, 479

[56] References Cited

U.S. PATENT DOCUMENTS

| | | | |
|---|---|---|---|
| 3,463,142 | 8/1969 | Harte | 128/633 |
| 4,166,695 | 9/1979 | Hill et al. | 356/28 |
| 4,223,680 | 9/1980 | Jobsis | 128/633 |
| 4,226,541 | 10/1980 | Tisue | 356/446 |
| 4,305,398 | 12/1981 | Sawa | 128/633 |
| 4,321,930 | 3/1982 | Jobsis et al. | 128/633 |
| 4,412,746 | 11/1983 | Yokouchi | 356/446 |
| 4,510,938 | 4/1985 | Jobsis et al. | 128/633 |
| 4,606,351 | 8/1986 | Lubbers | 128/633 |
| 4,655,225 | 4/1987 | Dahne et al. | 128/633 |
| 4,773,097 | 9/1988 | Suzaki et al. | 382/6 |
| 4,862,894 | 9/1989 | Fujii | 128/666 |
| 5,141,303 | 8/1992 | Yamamoto et al. | 351/211 |
| 5,224,478 | 7/1993 | Sakai et al. | 128/633 |
| 5,429,128 | 7/1995 | Cadell et al. | 128/633 |
| 5,517,987 | 5/1996 | Tsuchiya | 128/633 |
| 5,524,617 | 6/1996 | Mannheimer | 600/323 |

FOREIGN PATENT DOCUMENTS

92/16142  10/1992  WIPO .................................. 128/633

Primary Examiner—Eric F. Winakur
Attorney, Agent, or Firm—Nawrocki, Rooney & Sivertson, P.A.

[57] ABSTRACT

Apparatus and method for the monitoring of physiological parameters of a patient through the use of optical systems which do not require direct physical contact with the patient. The method and apparatus relate primarily to pulse oximetry for monitoring of pulse rate and arterial blood oxygen saturation. However, the apparatus and method of this invention are applicable to any form of optical detection of the physiological parameters in which light of any wavelength, visible or invisible, is directed from a remote instrument into a patient at a first imaging site, and subsequently collected at a second site spaced from the first site.

12 Claims, 5 Drawing Sheets

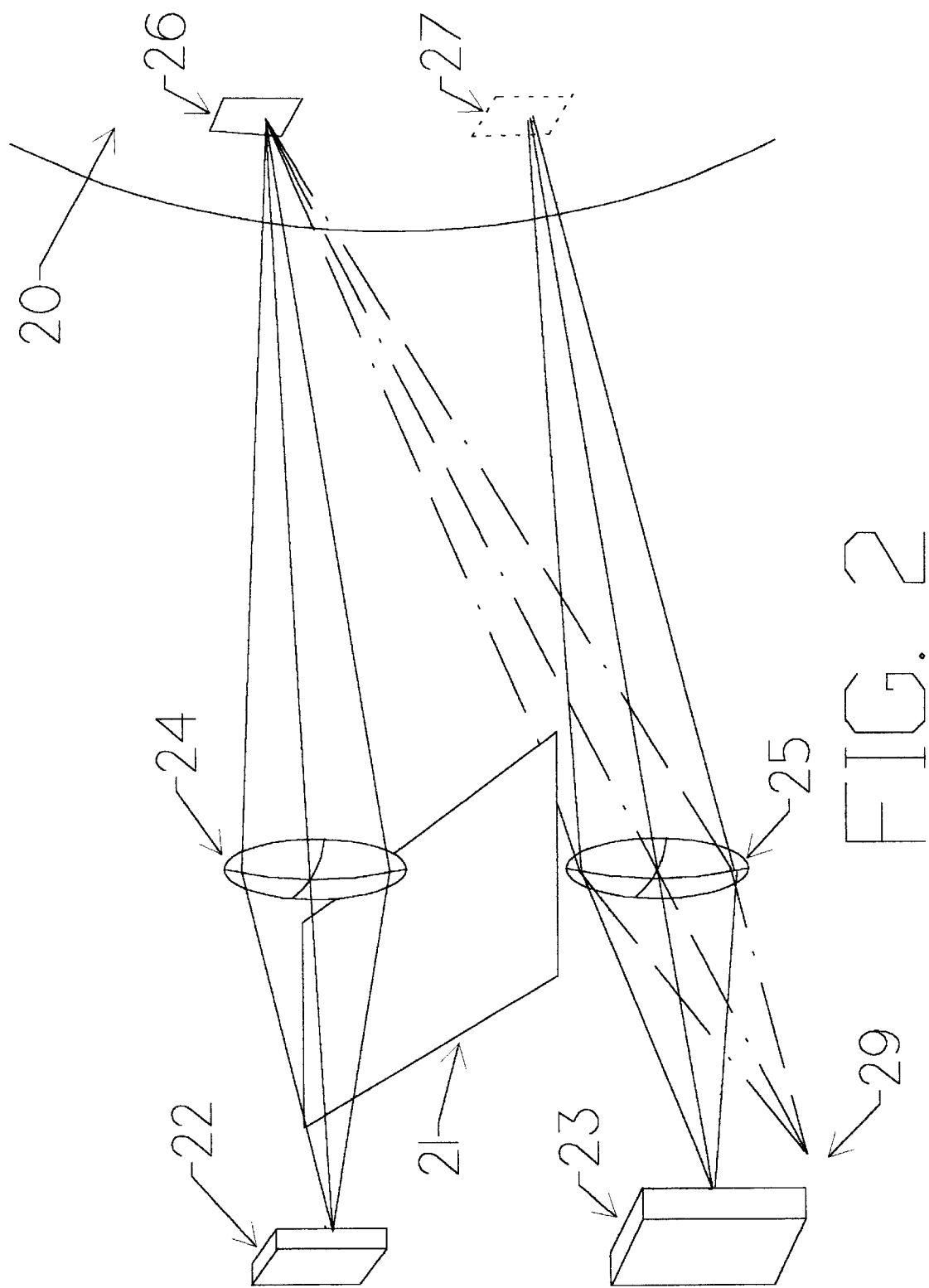

NON-CONTACT OPTICAL MONITORING OF PHYSIOLOGICAL PARAMETERS

CROSS REFERENCE TO CO-PENDING APPLICATIONS

U.S. patent application Ser. No. 08/490,315, filed Jun. 14, 1995, and entitled "Method and Apparatus for Removing Artifact and Noise from Pulse Oximetry", in the name of Thomas J. Yorkey, is commonly assigned with the instant invention and is incorporated herein by reference.

BACKGROUND OF THE INVENTION

1. Field of the Invention

This invention is concerned with apparatus and method for the monitoring of physiological parameters of a patient through the use of optical systems which do not require direct physical contact with the patient. More particularly, the method and apparatus described herein relates primarily to pulse oximetry for monitoring of pulse rate and arterial blood oxygen saturation. However, the apparatus and method of this invention are applicable to any form of optical detection of the physiological parameters in which visible or invisible light is directed into a patient and subsequently collected at a nearby location.

2. Description of the Prior Art

Pulse oximetry is generally well-known in the art. In presently-known conventional oximetry systems, light is provided from a source such as a pair of light-emitting diodes and is directed onto a pulsatile bed of tissue. The transmitted light is collected with a photodiode positioned on an opposite surface of the tissue bed in the case of transmission pulse oximetry, or on an adjacent surface of the tissue bed in the case of reflectance pulse oximetry. The light source and photodetector are generally housed in a reusable or a disposable sensor which connects to the pulse oximetry electronics and display unit. Photocurrents generated within the photodetector or light collector are detected and processed for measuring the relative amount of modulation of the transmitted red and near infrared light. It is well-known to those skilled in the art that the modulation ratio thus generated has been observed to have a high correlation with arterial oxygen saturation.

It is also well-known that accurate functioning of a pulse oximetry probe of the types presently in use requires that only light which has travelled through blood perfused tissues is collected at the sensor. Light which has not travelled through such blood perfused tissue, commonly called shunt or shunt light, causes an offset in the detected signal levels and results in an inaccurate estimate of oxygen saturation. Typical pulse oximetry sensors or probes are mounted directly on a surface of pulsatile tissue such as the finger, ear, foot or forehead of a patient. Shunt light is avoided through proper mechanical design and use of the sensor. In transmissive sensors, the emitter and detector are held against opposing surfaces of the pulsatile tissue bed so that the only light detected has necessarily travelled through the tissue. In reflectance sensors, shunts or shunt light are blocked from the sensor through the use of an opaque barrier positioned between the sensor's emitter and detector that can be pressed into or made to releasably adhere to the surface of the skin surrounding the pulsatile tissue bed.

It is thus obvious that a limitation in the use of conventional or presently-known transmissive or reflectance pulse oximetry is that the sensors all require physical contact with the patient. This contact is often inconvenient or undesirable in some patients. For example, some patients such as infants or burn victims, have fragile skin and cannot tolerate the mechanical or adhesive interaction required in the use of conventional probes. As another example, sleeping patients must generally be awakened to place the probes for a measurement of oxygen saturation. It has thus been apparent that a non-contact or remote form of pulse oximetry would be advantageous.

Prior art approaches to non-contact optical monitoring, and in particular pulse oximetry, have often related to the treatment of the eye where the advantage of not having to contact the retinal surface is obvious. Examples of prior art teachings relating to such non-contact optical monitors may be found in U.S. Pat. No. 4,305,398, issued to Sawa; U.S. Pat. No. 4,166,695, issued to Hill et al.; and U.S. Pat. No. 5,141,303, issued to Yamamoto et al. Each of these patents teaches the use of an optical system which yields reflected light information relating to the blood saturation of one or more portions of the eye. It should be noted that each of the systems taught by the prior art appear to have rather substantial mounts to assure the stability of the optical devices during measurement. Another form of non-contact optical measurement of physiological parameters is taught in U.S. Pat. No. 4,862,894, issued to Fujii. This patent teaches the use of a laser beam in combination with other optical devices for remote monitoring of the blood stream in a skin surface. This patent teaches a device which moves the laser beam across the skin causing it to image from a plurality of points which are arranged at least linearly. A light collector is provided to receive the laser beam's reflection which has been scattered by blood cells at the plurality of points on the surface of the skin.

SUMMARY OF THE INVENTION

The present invention differs from the prior art in that it provides a method and apparatus for monitoring physiological parameters such as oxygen saturation and pulse rate with pulse oximetry without the need to make physical contact with the patient, and by providing a shunt-free optical path through blood perfused tissue.

Briefly described, the present invention achieves the desired elimination of shunts from the collected light by having the light source illuminate a first area or region on a pulsatile bed of tissue, light from the light source travelling through selected optics to be imaged on the first area or region. The light source and the optics are remote from, that is, not in contact with, the selected tissue. The re-emitted light is then sensed from an area or region on the tissue bed which is selectively spaced from the first area such that the illuminated first area is not "visible" to the sensing or light collecting detectors. Thus, only deeply scattered light which penetrates into blood perfused tissue is collected. The shunt eliminating capability of the most preferred form of the present invention also enables the use of a motion correction algorithm which corrects for small movement of the remote or non-contact optical system, thus enabling, for example, the use of a hand-held oximetry probe.

Another advantage of the present invention is that by using remote technique problems extant with prior art contact devices are avoided. For example, forces applied on the tissue by contact devices may squeeze blood out of the tissue, resulting in the possibility that light may travel from the emitter to the detector through non-perfused tissue, thus causing measurement error. It is apparent that the remote device of the present invention does not apply any force on the tissue, and thus completely avoids this form of potential error.

BRIEF DESCRIPTION OF THE DRAWINGS

Other objects of the present invention and many of the attendant advantages of the present invention will be readily appreciated as they become better understood by reference to the following detailed description when considered in connection with the accompanying drawings, in which like reference numerals designate like parts throughout the figures thereof and wherein:

FIG. 2 is a schematic representation of the remote or non-contact monitoring apparatus of this invention;

DETAILED DESCRIPTION OF THE PREFERRED EMBODIMENTS

Figure 1A:
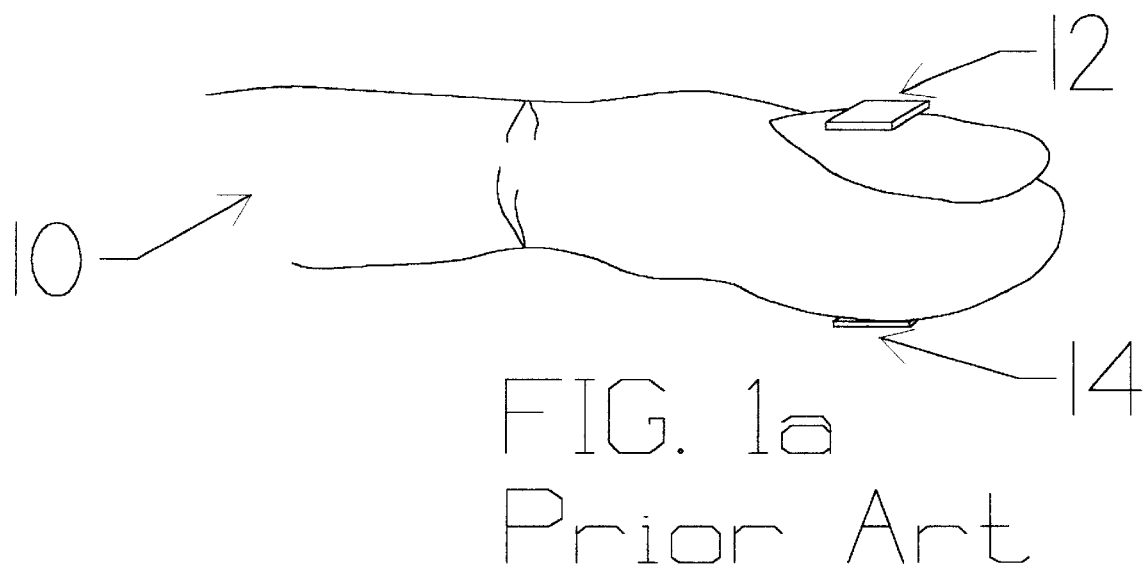
FIG. 1a and FIG. 1b depict, respectively, a prior art transmissive blood oximeter and a prior art reflective blood oximeter.

Referring to FIG. 1a, there is shown a prior art transmissive type blood oximetry device. In FIG. 1a there is shown a patient's finger indicated generally at 10. A light source 12 is mounted on one side of finger 10 and a light collector 14 is mounted on the opposite side of finger 10. Thus, the light provided by source 12 will travel through the tissue of finger 10 to be collected by device 14. The electronics for transmission and sensing of the light energy are well-known to those of skill in the art and have been omitted from FIG. 1a for purposes of clarity. Clearly both source 12 and detector 14 would be connected to operative electronics.

Figure 1B:
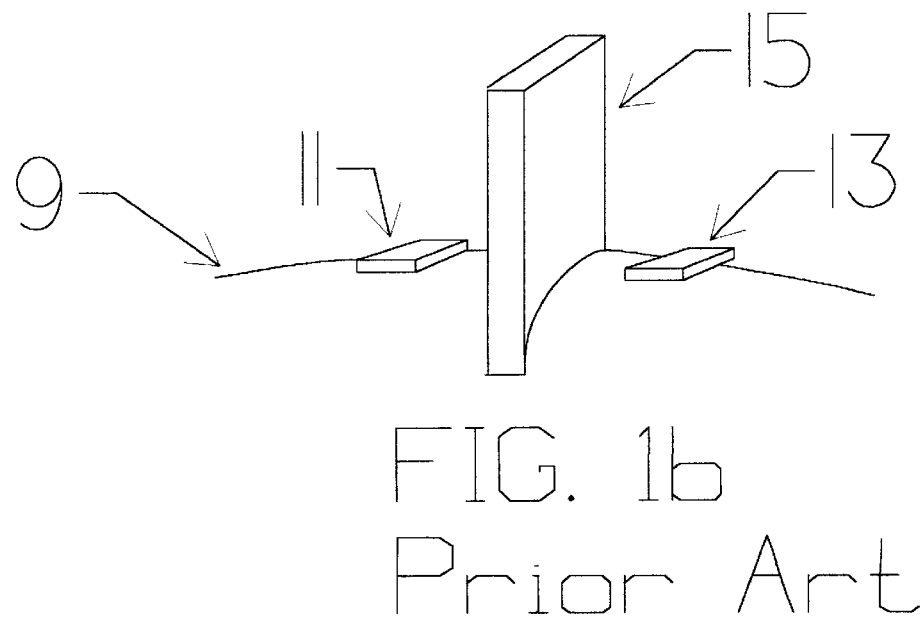

Referring now to FIG. 1b, there is shown a typical connection of a prior art reflective pulse oximetry. Here a pulsatile tissue bed is generally indicated as 9. A light source 11 is mounted in contact with one portion of tissue 9 and a light detector 13 is mounted in contact with the same surface of tissue 9, in spaced relation with source 11. In this form of pulse oximetry, light from source 11 travels into tissue 9 and detector 13 senses the re-emitted light after it passes through blood perfused tissue. An optical barrier 15 is shown mounted on the surface of tissue 9 between light source 11 and light detector 13 to prevent shunt light from being transmitted from device 11 to device 13, either directly through the air, or by reflection from the outside surface of the tissue. Again, the electronics for operation of devices 11 and 13 are well-known to those skilled in the art and have been left out of FIG. 1b for purposes of clarity.

Referring now to FIG. 2, there is shown a schematic representation of the remotely located optical physiological monitoring apparatus of this invention. A bed of pulsatile tissue indicated generally at 20 is shown as having a first area 26 to receive illumination from a light source 22, which source may be, for example, a set of light-emitting diodes or may be one or more lasers. The light from source 22 passes through a lens 24 to be delivered to area 26. The light from source 22 thus illuminating area 26 will be scattered throughout tissue 20 and much of it will be re-emitted through the surface of tissue 20 such as light which is re-emitted through a second region 27 on surface 20 spaced from first region 26. The re-emitted light at region 27 will have passed through the blood perfused tissue within bed 20 as is required for monitoring purposes. The re-emitted light from area 27 is collected by a lens 25 and presented to a light detector 23.

In FIG. 2 it can also be seen that shunt light from illuminated area 26 on tissue 20 (depicted by ghost lines) if collected by lens 25 will be imaged to a region, for example, the region generally indicated at 29, which is not visible to light detector 23. Thus, the apparatus of this invention prevents shunt light from the illuminated area and from areas other than imaged region 27 from interfering with detection of the desired re-emitted light signals.

It will be recognized that shunt light in the form of stray illumination light, due to reflections or imperfections in the optics of the illumination or collection sides of the system, must also be adequately eliminated to avoid error in the detection of the desired re-emitted light signals.

Also shown in FIG. 2 is an opaque member 21 mounted between lenses 24 and 25 to prevent direct shunt light from interfering in the optical process.

Not shown in FIG. 2 are the electronics which drive the illuminating portion of the present invention, namely, light source 22, and the electronics which process signals from the light collecting detector 23, as well as the computing and displaying electronics which are connected to make use of the data collected in device 23. These electronics are well-known to those of skill in the art and have been omitted from schematized FIG. 2 for the purposes of clarity.

Several embodiments of the present invention are possible, some of which will be described below in the discussion of FIGS. 3a–3d and FIG. 4, all of which share the basic principle shown and described with regard to FIG. 2 above; a photo-emitter such as 22, and a photodetector such as 23 are housed in a system which is located off the surface, that is, remote from the surface of the skin at a distance of from a few millimeters to many centimeters away depending on the optical design and practical considerations. This is accomplished by providing means for mounting the photo-emitter and photodetector not in contact with the tissue and remote therefrom, the means for mounting also not being in contact with the tissue and being remote therefrom.

Still referring to FIG. 2, the operating principle of the present invention utilizing a remote probe is clearly described. Light from source 22 is projected onto tissue bed 20 with a lens 24 and the re-emitted light is collected with a second lens 25 and projected into detector 23. Type I shunt light (light shunted entirely within the probe) is avoided by keeping the illumination side and the collection side of the apparatus of this invention separated with light barrier 21.

Type II shunt light (specular reflection or scattering from the surface of the tissue bed) is prevented by insuring that light emerging from region 26 cannot be imaged or scattered onto detector 23. Light from illuminated region 26 is imaged by lens 25 to strike the plane of detector 23 at a point 29 outside the aperture of detector 23 and is therefore not sensed.

For uses in which the separation distance between the apparatus of this invention and the patient varies during the measurement period, for example with a less than steady hand-held probe, a motion-correcting algorithm may be required. For heart rate monitoring this can be as simple as providing light source 22 with a plurality of wavelengths of light which are absorbed to a different degree by the pulsating arterial blood in the tissue bed 20. This plurality of signals can be sensed and a ratio taken to remove the motion artifact, as signals from each of the wavelengths of light are subject to substantially the same perturbations. This will become clear from the more complex three wavelength example described below.

It has been found that for pulse oximetry applications, three wavelengths of light are preferable utilizing the correction algorithm to be more fully described below. This algorithm assumes that light is coupled to tissue bed 20 with a certain degree of efficiency, and that this coupling efficiency may vary in magnitude at a frequency due to relative motion between instrument and patient, in a manner similar to, for example, the sensed plethysmogram from cardiac pulsations. This "motion noise" can be eliminated from the calculation of saturation if the relative degree of change in the coupling efficiency is the same for each of the wavelengths of light used. It is thus important in the design of the optical system for the remote probe of this invention that as the system-patient spacing varies, the illumination and collection efficiency for each light wavelength varies in a sufficiently similar manner for the motion-correcting algorithm to properly function. This too will be apparent from the discussion of the algorithm to follow.

FIGS. 3a–3d disclose four of the several embodiments of the apparatus of this invention for the purpose of illustrating that many alternate optical configurations and light sources may be used without departing from the spirit and scope of the present invention.

Each of FIGS. 3a–3d depicts a pulsatile tissue bed indicated generally at 30 and a remotely spaced probe of varying designs for utilizing the principles of the present invention to monitor physiological events within tissue 30.

Figure 3A:
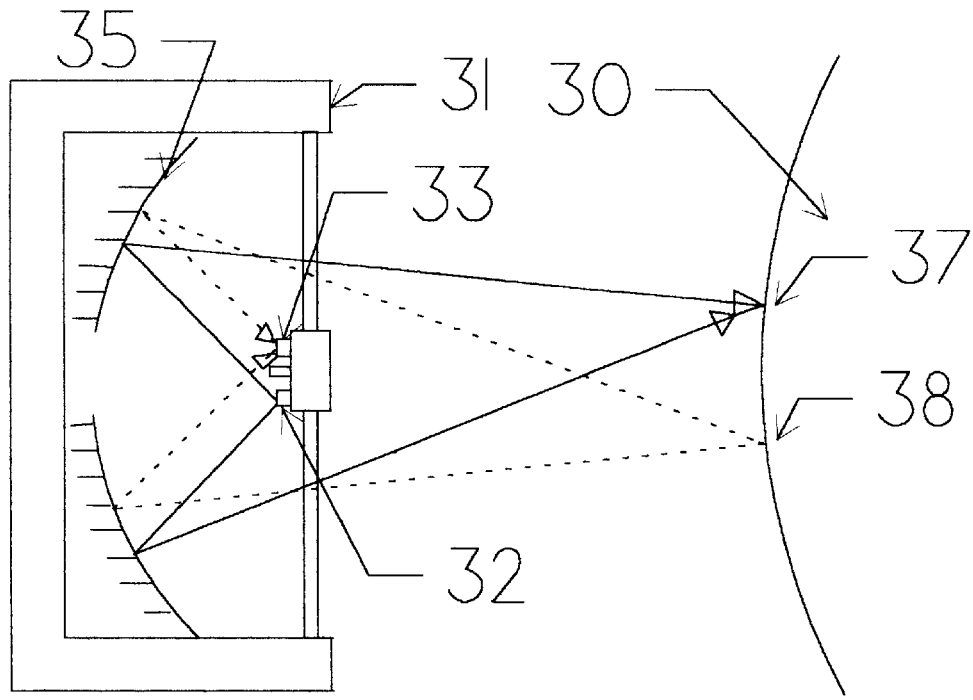
FIGS. 3a, 3b, 3c and 3d schematically represent various embodiments of apparatus for achieving the teachings of the present invention.

Referring to FIG. 3a, there is shown a housing 31 in which are mounted an annular concave mirror 35, a light source 32 which preferably contains three light-emitting diodes, and a photodetector 33. The separate wavelengths from light source 32 are reflected by mirror 35 to illuminate a first region 37 on tissue 30. Re-emitted light (shown in ghost lines) from a second region or area 38 on tissue 30 is collected by mirror 35 and presented to photodetector 33. Concave mirror 35 is annular in shape so as to not directly reflect light from emitter 32 onto detector 33.

Figure 3B:
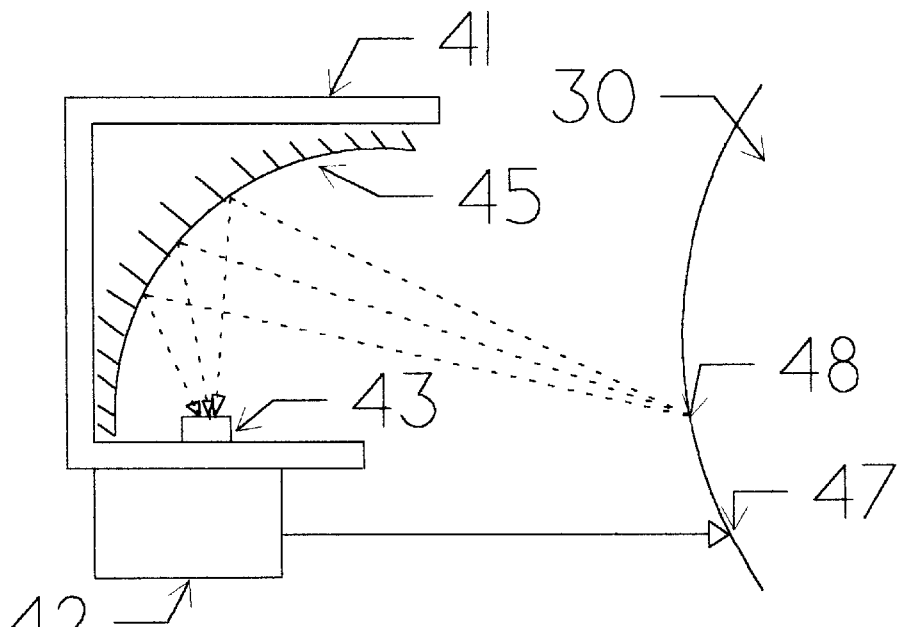

In FIG. 3b, there is shown a housing 41 which contains an elliptical mirror 45. Also mounted on housing 41 are a light source 42, preferably a laser source providing three wavelengths of light, which source could be three lasers of different wavelengths (see the discussion of FIG. 4), and a photodetector 43. The three wavelength laser source from device 42 illuminates a first region 47 on tissue 30. Re-emitted light from a second region 48 on tissue 30 is collected by mirror 45 and presented to photodetector 43.

Figure 3C:
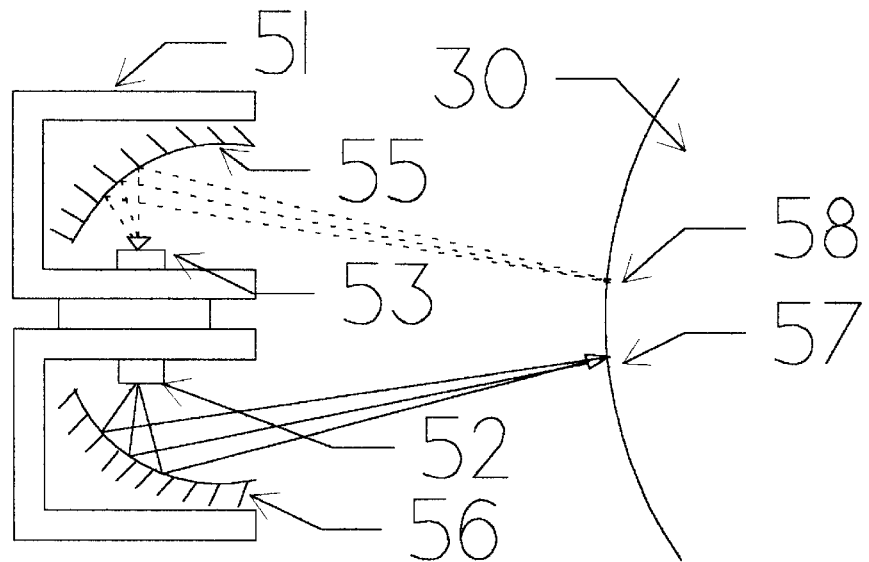

FIG. 3c shows a casing 51 having an upper and lower section. The lower section of casing 51 includes an elliptical mirror 56 and a light source 52 preferably comprising three light-emitting diodes. The upper section of casing 51 includes another elliptical mirror 55 and a photodetector 53. In operation light source 52 provides three wavelengths of light which are imaged by mirror 56 to illuminate a first region 57 on tissue 30. A second region 58 on tissue 30 provides re-emitted light from tissue 30 to mirror 55 which then presents the light to light detector 53.

Figure 3D:
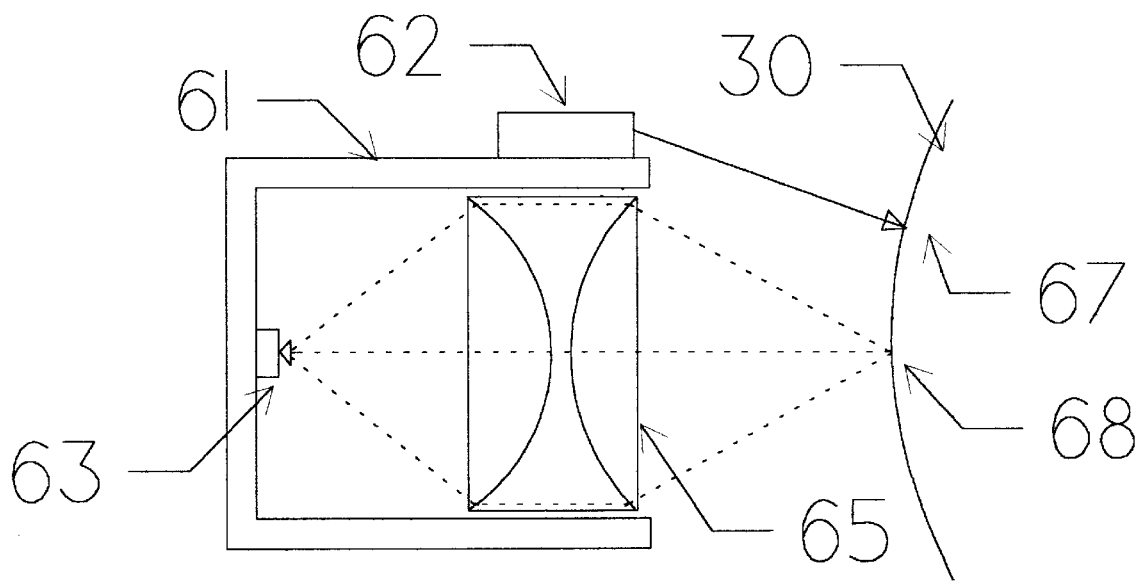

FIG. 3d discloses a casing 61. A laser light source 62, preferably a three wavelength laser source, is mounted on casing 61. Also mounted in casing 61 is a lens 65, which is preferably an antireflection (AR) coated lens to minimize shunting from ghost images, and may preferably be one of a number of known types of lenses such as an air-spaced condenser, a Fresnel lens, or a cemented achromatic doublet. A photodetector 63 is also mounted in casing 61. The three wavelength laser beam from source 62 illuminates a first region 67 on tissue 30. A second region 68 on tissue 30 is selected to provide re-emitted light from tissue 30 to lens 65, and thence to detector 63.

In each of the above four embodiments of FIGS. 3a–3d, the illumination of tissue 30 occurs several millimeters away from the region that is within the view of the photodetector; for example region 37 is spaced from region 38 in FIG. 3a, region 47 is spaced from region 48 in FIG. 3b, region 57 is spaced from region 58 in FIG. 3c, and region 67 is spaced from region 68 in FIG. 3d; thus, specular reflections from the skin, as well as light that has scattered only superficially from non-perfused tissue, is imaged outside the detector aperture, thus avoiding shunt light.

Another feature common to the four embodiments of FIGS. 3a–3d is that the coupling geometry between the optical system and the patient is essentially equivalent for the three wavelengths of light used, thereby assuring that any changes in coupling efficiency will be substantially the same for each wavelength, thus satisfying the requirements of the motion correcting algorithm more fully discussed below.

By way of example, the three wavelength light emitting diode source in the examples of FIGS. 3a and 3c may be fabricated by placing the three individual dies close to one another on a common substrate, for example on a four-lead TO-46 header. The three wavelength laser assembly of FIGS. 3b and 3d may preferably comprise three laser beams made substantially collinear using dichroic beam splitters or with multiple mirrors, in a manner well-known to those of skill in the art.

Figure 4:
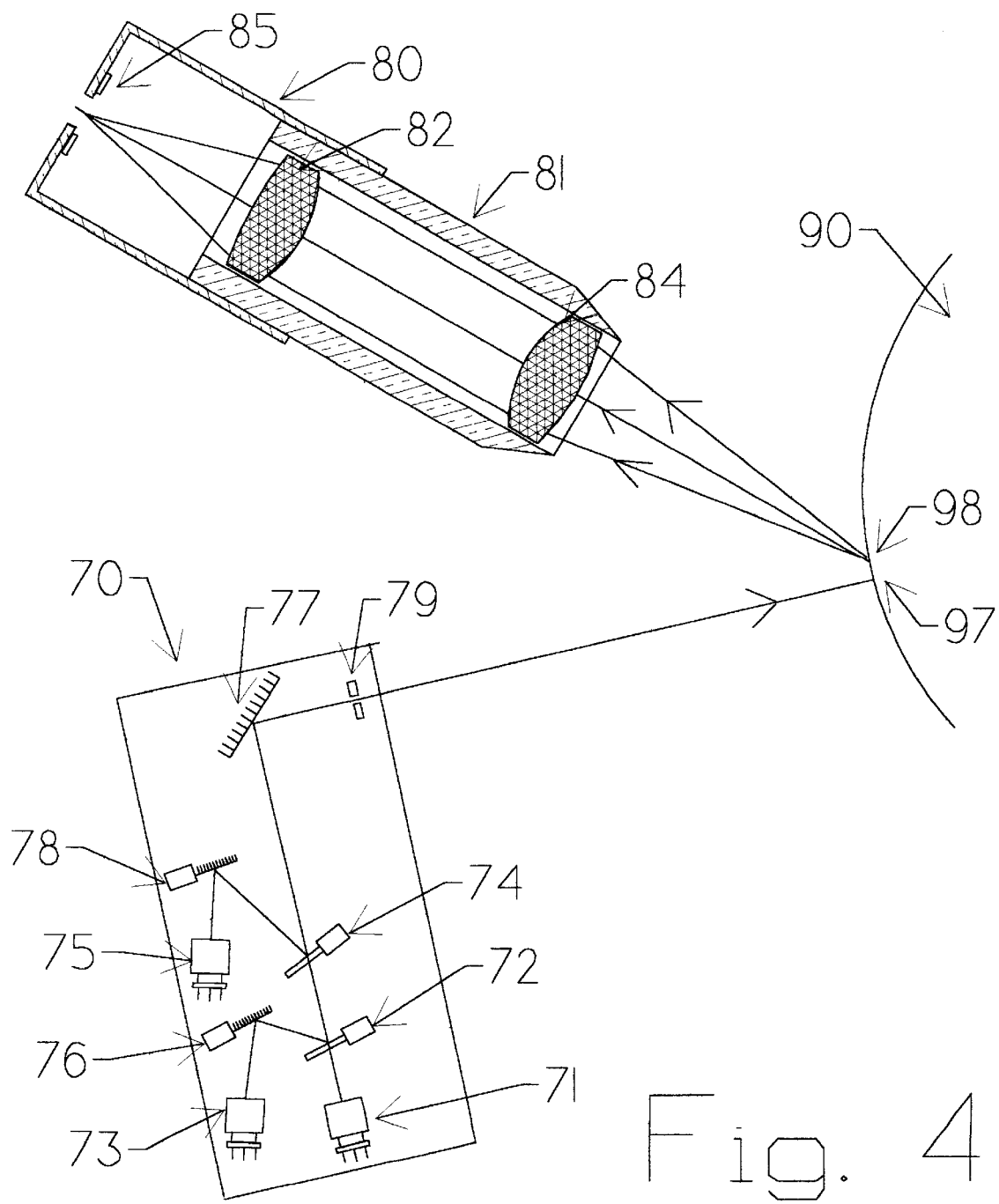
FIG. 4 is a more detailed schematic representation of a preferred embodiment of this invention.

Referring now to FIG. 4 there is shown a schematic version of a preferred embodiment of this invention that uses an annular photodetector to increase detection efficiency. FIG. 4 also shows the preferred three laser illuminating device described above in a more detailed schematic.

FIG. 4 discloses a light director indicated generally at 70. Director or illuminator 70 includes three laser diodes and associated collimating optics 71, 73 and 75. Also shown are a pair of interference filters 72 and 74, each with an adjustable filter mount. Also shown are a pair of mirrors 76 and 78, each with an adjustable mirror mount. Further depicted in light director 70 is a mirror 77 and a pinhole assembly 79.

A light detector housing is indicated generally at 80, and housing 80 is shown as including a lens housing indicated generally at 81. Lens housing 81 has mounted therein a pair of lenses 82 and 84. Detector or light collector housing 81 has mounted therein a light collector 85, which collector 85 in this embodiment of FIG. 4 preferably comprises an annular photodetector.

FIG. 4 also depicts a pulsatile tissue bed or other physiological sample 90, including an illumination imaging site 97 and a spaced light-re-emitting site 98 which may be an annulus. The operation of the apparatus of FIG. 4 is similar to that of FIGS. 3a–3d described above. In FIG. 4 diodes 71, 73 and 75, may be selected to be, respectively, an 840 nm laser diode, a 790 nm laser diode and a 670 nm laser diode. The desired three wavelengths will thus be present. The beam from diode 71 is passed through interference filter 72 which is preferably an 800 nm long pass filter. The beam from diode 73 is directed to filter 72 by mirror 76 where it is not passed, but is reflected to join with the passed beam from diode 71, and the joined pair are then passed through interference filter 74 (700 nm long pass filter). The beam from diode 75 is reflected by mirror 78 to filter 74 where it is not passed, but is reflected to join with the pair of beams from diodes 71 and 73. The collinear three wavelength light beam thus formed is directed to mirror 77 where it is reflected through pinhole 79 (preferably having approximately a 0.6 mm diameter) to illuminate site 97. Pinhole 79 functions to minimize stray light reflections within enclosed optical housing 70 from reaching the patient's tissue.

As can be seen in FIG. 4, the re-emitted light from site 98 is collected and imaged by lenses 84 and 82, and thence, directed to annular photodetector 85. The signal detected by photodetector 85 is then presented to computing and displaying electronics (not shown.) The image of illumination site 97 falls within the center of the annular photodetector 85, and hence, does not cause shunt light signals.

THREE WAVELENGTH MOTION CORRECTION ALGORITHM FOR PULSE OXIMETRY

Following the Beer-Lambert Law model for approximating the behavior of pulse oximetry, let $$I_1 = I_{10} \cdot \eta_1(d[t]) \cdot exp(-\beta_1 Cl) \tag{A1}$$

$$I_2 = I_{20} \cdot \eta_2(d[t]) \cdot exp(-\beta_2 Cl) \tag{A2}$$

$$I_3 = I_{30} \cdot \eta_3(d[t]) \cdot exp(-\beta_3 Cl) \tag{A3}$$

where $I_1$ signifies the detected signal intensity at wavelength 1; $I_{10}$, the intensity of the light source at wavelength 1; $\eta_1(d[t])$, the time dependent component of the coupling efficiency between the optical system and the tissue bed at wavelength 1; $\beta_1$, the extinction coefficient of the arterial blood at wavelength 1; C is the time dependent concentration of arterial blood in the tissue; and l is the path length traveled by the light in the tissue. Subscripts 2 and 3 refer to wavelengths 2 and 3, respectively. It should be noted that there may be non-time-dependent differences in the coupling efficiencies and, for the purpose of this analysis, such differences may be included by appropriate changes to $I_{10}$, $I_{20}$, and $I_{30}$. When this has been done, there will be a point in time at which $\eta_1 = \eta_2 = \eta_3 = 1$. The subsequent discussion will show that it is important for any time-dependent changes in $f_1$, $\eta_2$, and $\eta_3$ to be similar, though not necessarily exactly equal. Note that $$\beta_n = S \cdot \beta_n^{oxy} + (1-S) \cdot \beta_n^{red} \tag{A4}$$

with n referring to wavelengths 1, 2, and 3; S is the oxygen saturation of arterial blood ($0 \leq S \leq 1$), and $\beta_n^{oxy}$ and $\beta_n^{red}$ are the extinction coefficients for oxygenated and reduced hemoglobin, respectively, at wavelength n. Taking the natural logarithm of equations A1–A3, and then taking the time derivative of each equation, it follows that:

$$ln(I_n) = ln(I_{no}) + ln(\eta_n(d[t])) - \beta_n Cl \tag{A5}$$

$$d/dt\{ln(I_n)\} = d/dt\{ln(\eta_n(d[t]))\} - \beta_n \cdot l \cdot dC/dt \tag{A6}$$

If we can make the assumption that $\eta_1(d[t]) = \eta_2(d[t]) = \eta_3(d[t])$, or that these values are sufficiently equal to provide the required accuracy, and that the source intensities are constant, that is, $d/dt(I_{no}) = 0$, then the differences between equation A6 evaluated for wavelengths 1 and 3, and wavelengths 2 and 3 become $$d/dt\{ln(I_3)\} - d/dt\{ln(I_1)\} = -(\beta_3 - \beta_1) \cdot l \cdot dC/dt \tag{A7}$$

$$d/dt\{ln(I_3)\} - d/dt\{ln(I_2)\} = -(\beta_3 - \beta_2) \cdot l \cdot dC/dt \tag{A8}$$

Taking the ratio of equations A7 and A8, and making the substitution of equation A4, it follows:

$$R = \frac{d/dt\{ln(I_3)\} - d/dt\{ln(I_1)\}}{d/dt\{ln(I_3)\} - d/dt\{ln(I_2)\}} \tag{A9}$$

$$R = \frac{S \cdot (\beta_3^{oxy} - \beta_1^{oxy}) + (1-S) \cdot (\beta_3^{red} - \beta_1^{red})}{S \cdot (\beta_3^{oxy} - \beta_2^{oxy}) + (1-S) \cdot (\beta_3^{red} - \beta_2^{red})} \tag{A10}$$

This result is independent of the time (motion) dependent coupling efficiency $\eta$, as well as dC/dt and l, as they are considered equivalent at the three wavelengths in the Beer-Lambert model. Equation A10 can be solved for saturation (S) as a function of the measured value R in the same manner as is done in the conventional two wavelength pulse oximeter. This leaves:

$$S = \frac{(\beta_3^{red} - \beta_1^{red}) - R \cdot (\beta_3^{red} - \beta_2^{red})}{R \cdot \{(\beta_3^{oxy} - \beta_2^{oxy}) - (\beta_3^{red} - \beta_2^{red})\} + (\beta_3^{red} - \beta_1^{red}) - (\beta_3^{oxy} - \beta_1^{oxy})} \tag{A11}$$

If we create difference coefficients for oxygenated and reduced hemoglobin, $$\Delta\beta_1 = \beta_3 - \beta_1 \tag{A12}$$

$$\Delta\beta_2 = \beta_3 - \beta_2 \tag{A13}$$

then equation A11 can be rewritten as $$S = \frac{\Delta\beta_1^{red} - R \cdot \Delta\beta_2^{red}}{R \cdot (\Delta\beta_2^{oxy} - \Delta\beta_2^{red}) + \Delta\beta_1^{red} - \Delta\beta_1^{oxy}} \tag{A14}$$

As in conventional two wavelength pulse oximetry, the four constants in equation A14 are empirically determined in calibrating the oximeter. Those of skill in the art will readily recognize that other motion correcting algorithms may be used while still being within the scope of this invention.

What is claimed is:

1. A method of remotely monitoring a characteristic of arterial blood in pulsatile tissue, comprising the steps of:
   providing a light source including optics for illuminating a first area of tissue, a light detector including collection optics for collecting essentially only re-emitted light from a second area of the tissue spaced a predetermined distance from said first area, and means for mounting the light source and light detector remotely from the pulsatile tissue;
   positioning said mounting means remotely from the first and second areas of tissue and tissue adjacent thereto;
   projecting light from the light source on the first area of tissue;
   collecting light with the light detector from the second area of tissue; and
   calculating the characteristic of the arterial blood in the pulsatile tissue using a first step which separates time dependent from non-time dependent collected light intensities and a second step which utilizes said time dependent light intensities to calculate the characteristics of the arterial blood in the pulsatile tissue.

2. The method of claim 1 wherein said collection optics includes imaging means for preventing reemitted light from said first area from reaching said light detector.

3. The method of claim 1, wherein said light source provides light at a plurality of wavelengths, and said detector senses each of said plurality of wavelengths.

4. The method of claim 3, further comprising providing computation means connected to said light detector for calculating a motion correction algorithm from said sensed plurality of wavelengths and measuring variable portions of amplitudes of said wavelengths and plurality of with the computation means wavelengths.

5. The method of claim 1, further comprising compensating for relative motion between the tissue and either of the light source or the light detector by the steps of measuring amplitudes and calculating a ratio of collected light of at least two different wavelengths.

6. The method of claim 1, wherein the light source and light detector are positioned to prevent light shunt.

7. Apparatus for remotely monitoring a characteristic of arterial blood in pulsatile tissue, said apparatus comprising:
   a) a light source having optic means for illuminating a first area of tissue;
   b) a light detector having collection optic means for collecting essentially only re-emitted light from a second area of the tissue spaced a predetermined distance from said first area; said light source and said light detector having mounting means for mounting said light source and said light detector remotely from the pulsatile tissue, with said mounting means being positioned remotely from the first and second areas of tissue and tissue adjacent thereto; and
   c) calculating means for calculating the characteristic of the arterial blood in the pulsatile tissue by separating time dependent from non-time dependent light intensities sensed by said light detector and utilizing said time dependent light intensity information to determine the characteristics of the arterial blood in the pulsatile tissue.

8. The apparatus of claim 7, wherein said collection optic means further comprises imaging means for preventing reemitted light from said first area from reaching said light detector.

9. The apparatus of claim 7, wherein said light source provides light at a plurality of wavelengths, and wherein said light detector senses each of said plurality of wavelengths.

10. The apparatus of claim 9, wherein said calculating means further comprises means for implementing a computational algorithm utilizing signals from said light detector sensed plurality of wavelengths that compensates for relative motion between the mounting means and the tissue by determining amplitudes of said plurality of wavelengths, calculating ratios of variable portions of said amplitudes, and comparing the ratios of the variable portions.

11. The apparatus of claim 7, wherein said calculating means further comprises means for compensating for relative motion between the tissue and either of the light source or the light detector by determining and utilizing a ratio of collected light from at least two different wavelengths.

12. The apparatus of claim 7, wherein said light source and said light detector are positioned to prevent light shunt.

* * * * *